United States Patent [19]
Plank et al.

[11] 3,992,466
[45] Nov. 16, 1976

[54] HYDROCARBON CONVERSION

[75] Inventors: Charles J. Plank, Woodbury; Edward J. Rosinski, Pedricktown, both of N.J.; Albert B. Schwartz, Philadelphia, Pa.

[73] Assignee: Mobil Oil Corporation, New York, N.Y.

[22] Filed: Aug. 13, 1975

[21] Appl. No.: 604,296

[52] U.S. Cl. .................... 260/671 C; 208/111; 208/135; 252/455 Z; 260/668 A; 260/683.15 R; 423/328
[51] Int. Cl.² .................. C10G 35/06; C10G 13/02; C07C 3/50
[58] Field of Search... 260/668 A, 671 C, 683.15 R; 208/DIG. 2, 111, 135

[56] References Cited
UNITED STATES PATENTS

| | | |
|---|---|---|
| 3,728,408 | 4/1973 | Tobias............................. 260/671 C |
| 3,761,389 | 9/1973 | Rollmann........................ 260/671 C |
| 3,855,115 | 12/1974 | Morrison ............................ 208/135 |
| 3,926,782 | 12/1975 | Plank et al.......................... 208/135 |

Primary Examiner—Delbert E. Gantz
Assistant Examiner—C. E. Spresser
Attorney, Agent, or Firm—Charles A. Huggett; Raymond W. Barclay

[57] ABSTRACT

This invention relates to a process for converting hydrocarbons in the presence of a catalyst comprising a ZSM-35 crystalline aluminosilicate, which zeolite, as crystallized, is in the form of very small particles having diameters, in the range of 0.005 micron to 0.1 micron. The use of such small crystalline ZSM-35 zeolite as catalyst in hydrocarbon conversion serves to retard catalyst aging during the hydrocarbon conversion reaction.

9 Claims, No Drawings

HYDROCARBON CONVERSION

CROSS REFERENCE TO RELATED APPLICATION

This application is related to copending application Ser. No. 330,925 filed Feb. 9, 1973 now U.S. Pat. No. 3,926,782 issued Dec. 16, 1975.

BACKGROUND OF THE INVENTION

1. Field of the Invention

This invention relates to hydrocarbon conversion in the presence of a crystalline aluminosilicate catalyst. More particularly, this invention relates to a process for converting hydrocarbons with a catalyst of ZSM-35 zeolite having an ultimate particle diameter of 0.005 to 0.1 micron as crystallized.

2. Description of the Prior Art

The crystalline aluminosilicate zeolite ZSM-35 and conversion of hydrocarbons in the presence thereof is more particularly described in U.S. application Ser. No. 528,061, filed Nov. 29, 1974, the entire contents of which are incorporated herein by reference. This zeolite, as synthesized, can be identified, in terms of mole ratios of oxides and in the anhydrous state, as follows:

$$(0.3-2.5) R_2O : (0-0.8) M_2O : Al_2O : Al_2O_3 : > 8 SiO_2$$

wherein R is an organic nitrogen-containing cation derived from ethylenediamine or pyrrolidine and M is an alkali metal cation, and is characterized by a specified X-ray powder diffraction pattern. Catalyst containing ion exchanged ZSM-35 crystals have been found to be useful in petroleum processes such as upgrading the octane number of naphthas and reformates, catalytic dewaxing of petroleum fractions, reduction in the pour point of distillate and residual fuel oils, reduction in the freeze point of jet fuels, alkylation of aromatics with olefins, aromatization of normally gaseous olefins and paraffins, aromatization of normally liquid low molecular weight parrafins and olefins, isomerization of aromatics, paraffins and olefins, disproportionation of aromatics, transalkylation of aromatics, oligomerization of olefins and as a component for cracking catalyst. All of the foregoing catalytic processes are of value since they result in upgrading of the hydrocarbon charge being processed.

Along with other zeolite catalysts, those containing ZSM-35 have experienced a decline in catalytic activity with the duration of their use. Those skilled in the art of petroleum processing have sought means for extending the useful life of zeolite-containing catalysts. It would, as those in the art are aware, be of considerable practical advantage to retard the aging of a ZSM-35 containing zeolite catalyst during its use in hydrocarbon processing.

SUMMARY OF THE INVENTION

In accordance with the invention described herein, the use of ZSM-35 zeolite, characterized by an ultimate particle diameter of 0.005 to 0.1 micron when crystallized, as the catalyst serves to retard aging of such catalyst during operations involving catalytic processing of hydrocarbon charge stocks carried out in the presence of ZSM-35 containing catalyst.

Crystalline aluminosilicate zeolite ZSM-35, as above noted, is identified as synthesized, in terms of mole ratios of oxides and in the anhydrous state, as follows:

$$(0.3-2.5) R_2O : (0-0.8) M_2O : Al_2O_3 : > 8 SiO_2$$

wherein R is an organic nitrogen-containing cation derived from ethylenediamine or pyrrolidine and M is an alkali metal cation, and is characterized by a specified X-ray powder diffraction pattern. The term "anhydrous" as used in the above context means that molecular water is not included in the formula.

The original cation can be replaced in accordance with techniques well known in the art, at least in part, by ion exchange with other cations. Preferred replacing cations include alkylammonium cations, metal cations, ammonium ions, hydrogen ions and mixtures of the same. Particularly preferred cations are those which render the zeolite catalytically active. These include hydrogen, rare earth metals, aluminum, metals of Groups II and VIII of the Periodic Table and manganese. Especially preferred is ZSM-35 in the acid form. Also desired are zeolites which are thermally treated products of the foregoing, said thermal treatment consisting of heating the ZSM-35 type zeolite in the desired particular cation form at a temperatutre of at least 700° F.

In a preferred synthesized form, the zeolite has a formula, in terms of mole ratios of oxides and in the anhydrous state, as follows:

$$(0.4-2.5) R_2O : (0-0.6) M_2O : Al_2O_3 : xSiO_2$$

wherein R is an organic nitrogen-containing cation derived from ethylenediamine or pyrrolidine, M is an alkali metal, especially sodium, and x is from greater than 8 to about 50.

The synthetic ZSM-35 zeolite possesses a definite distinguishing crystalline structure whose X-ray diffraction pattern shows substantially the significant lines set forth in Table I. It is observed that this X-ray diffraction pattern (with respect to significant lines) is similar to that of natural ferrierite with a notable exception being that natural ferrierite patterns exhibit a significant line at 11.33A. Close examination of some individual samples of ZSM-35 may show a very weak line at 11.3–11.5A. This very weak line, however, is determined not to be a significant line for ZSM-35.

TABLE I

| d(A) | I/Io |
|---|---|
| 9.6 ± 0.20 | Very Strong - Very Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |
| 3.14 ± 0.06 | Weak Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |

TABLE I-continued

| d(A) | I/Io |
|---|---|
| 2.48 ± 0.05 | Weak |

A further characteristic of ZSM-35 is its sorptive capacity proving said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane for ZSM-35 (after calcination at 600° C.) is less than 10 whereas that ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing compound, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH⁻/SiO₂ | 0.05–0.5 | 0.07–0.49 |
| H₂O/OH⁻ | 41–500 | 100–250 |
| SiO₂/Al₂O₃ | 8.8–200 | 12–60 | wherein R is an organic nitrogen-containing component derived from pyrrolidine or ethylenediamine and M is an alkali metal ion, and maintaining the mixture until crystals of the zeolite are formed. (The quantity of OH⁻ is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g. at 230° F., for from about 8 to 24 hours.

To produce very small ZSM-35 crystals in the range of 0.005 to 0.1 micron in ultimate particle diameter, high speed stirring and concomitant high mass transfer rates during production of the crystals is carried out. The crystalline product of such small size range may be loosely agglomerated without detrimental effects. Typical conditions maintained during crystallization include a temperature in the range of 75° C. to 205° C. for a period of time from 1 hour to 60 days. Preferably, the temperature is maintained in the range of about 90° C. to about 175° C. up to about 10 days while stirring.

ZSMk-35 zeolites can be prepared utilizing materials which supply the appropriate oxide. Such compositions include sodium aluminate, sodium silicate, silica hydrosol, silica gel, silicic acid and sodium hydroxide. The nitrogen-containing cation can be derived from either pyrrolidine or ethylenediamine. It will be understood that each oxide component utilized in the reaction mixture for preparing ZSM-35 can be supplied by one or more initial reactants and they can be mixed together in any order. For example, sodium oxide can be supplied by an aqueous solution of sodium hydroxide or by an aqueous solution of sodium silicate.

ZSM-35 zeolites can have the original cations associated therewith replaced by a wide variety of other cations according to techniques well known in the art. Typical replacing cations would include hydrogen, ammonium, and metal cations including mixtures of the same. Of the replacing metallic cations, particular preference is given to cations of metals such as rare earth metals, manganese, calcium, as well as metals of Group II of the Periodic Table, e.g. zinc and Group VIII of the Periodic Table, e.g. nickel.

Typical ion exchange techniques would be to contact the ZSM-35 zeolite before or after calcination with a salt of the desired replacing cation or cations. Although a wide variety of salts can be employed, particular preference is given to chlorides, nitrates and sulfates.

Representative ion exchange techniques are disclosed in a wide variety of patents including U.S. Pat. Nos. 3,140,249; 3,140,251 and 3,140,253.

Following contact with the salt solution of the desired replacing cation, the zeolites are then preferably washed with water and dried at a temperature ranging from 150° F. to about 600° F. and thereafter calcined in air, steam, inert gases or mixtures thereof at temperatures ranging from about 500° F. to 1600° F. for periods of time ranging from 1 to 48 hours or more.

In the case of many catalysts, it is desired to incorporate the ZSM-35 with another material resistant to the temperatures and other conditions employed in organic conversion processes. Such materials include active and inactive materials and synthetic or naturally occurring zeolites as well as inorganic materials such as clays, silica and/or metal oxides. The latter may be either naturally occurring or in the form of gelatinous precipitates or gels including mixtures of silica and metal oxides. Use of a material in conjunction with the ZSM-35, i.e., combined therewith which is active, tends to improve the conversion and/or selectivity of the catalyst in certain organic conversion processes. Inactive materials may suitably serve as diluents to control the amount of conversion in a given process so that products can be obtained economically and orderly without employing other means for controlling the rate of reaction. Normally, zeolite materials have been incorporated into naturally occurring clays, e.g., bentonite and kaoline, to improve the crush strength of the catalyst under commercial operating conditions. These materials, i.e., clays or inorganic oxide, function, in part, as binders for the catalyst. It is desirable to provide a catalyst having good crush strength, because in a petroleum refinery the catalyst is often subjected to rough handling, which tends to break the catalyst down into powder-like materials which cause problems in processing. These clay binders have been employed for the purpose of improving the crush strength of the catalyst.

Naturally occurring clays which can be composited with the ZSM-35 catalyst include those of the montmorillonite and kaolin family, which families include the sub-bentonites, and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the ZSM-35 catalyst can be composited with a porous matrix material such as alumina, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel, metal oxide slurry or powder. The relative proportions of finely divided crystalline aluminosilicate ZSM-35 and inorganic oxide matrix may vary widely with the crystalline aluminosilicate content ranging from about 1 to about 90 percent by weight and more usually, from about 2 to about 70 percent by weight of the composite. The product can be in form of beads, extrudates, tablets, spray dried spheroids or granules, suitable for use in fixed bed, moving bed or fluid bed.

ZSM-35 zeolites can be used either in the alkali metal form (e.g., the sodium form), the ammonium form, the hydrogen form, or another univalent or multivalent cationic form. Preferably, forms other than those of the alkali metals are employed. They can also be used in intimate combination with a hydrogenating component such as tungsten, vanadium, molybdenum, rhenium, nickel, coablt, chromium, manganese or a noble metal such as platinum or palladium where a hydrogenation/-dehydrogenation function is to be performed. Such component can be exchanged into the composition, impregnated therein or physically intimately admixed therewith. Such component can be impregnated in or on to ZSM-35 such as, for example, by, in the case of platinum, treating the zeolite with a platinum metal-containing ion. Thus, suitable platinum compounds include chloroplatinic acid, platinous chloride and various compounds containing the platinum amine complex.

Use of the very small crystalline size ZSM-35 containing catalyst, i.e. 0.005 to 0.1 micron in diameter, is, in accordance with the present invention, contemplated to result in retardation of aging of such catalyst during various hydrocarbon conversion reactions including upgrading of reformate, transalkylation of aromatic hydrocarbons, alkylation of aromatics, reduction in pour point of fuel oils, oligomerization of olefins and in catalytic cracking of hydrocarbons. Exemplary of such processes is the upgrading of naphthas or reformates. The use of the small crystallite size ZSM-35 catalyst in such operation is contemplated not only to result in retarding the aging of the ZSM-35 catalyst but also may give rise to improved yield-octane through use of decreased hydrogen/hydrocarbon ratio while retaining satisfactory aging during naphtha or reformate processing. Oligomerization of olefins, i.e. olefins having 2 to 10 carbon atoms is effectively carried out with the small crystallite size ZSM-35 containing catalyst. Such rection is suitably effected at a temperature between about 550° F and about 1150° F., a pressure between about 0.01 and about 1000 psig utilizing a weight hourly space velocity within the approximate range of 0.1 to 1000. Alkylation of aromatic hydrocarbons, e.g. benzene, with an alkylating agent such as an alkyl halide, an alcohol or an olefin, is also readily effected in the presence of the small crystallite size ZSM-35 containing catalyst with reduced aging. Alkylation conditions include a temperature between about 400° and about 1000° F., a pressure between about 25 and about 1000 psig utilizing an aromatic hydrocarbon/alkylating agent mol ratio of 2 to 200 and an alkylating agent weight hourly space velocity within the approximate range of 0.5 to 50. Ortho-xylene isomerization is another reaction suitably conducted in the presence of the small crystallite size ZSM-35. Isomerization conditions include a temperature between about 300° and about 900° F., a pressure between about 25 and about 1000 psig utilizing a weight hourly space velocity within the approximate range of 0.2 to 100.

Thus, in accordance with the process of the present invention, the use of very small ZSM-35 crystallites, 0.005 to 0.1 micron in ultimate particle diameter, results in retarding the aging of catalysts containing such ZSM-35 crystals during hydrocarbon processing. As noted hereinabove, the extremely small crystalline size of ZSM-35 may be achieved as a result of high speed stirring to give high mass transfer rates and high shear of the reaction mixture during the process of crystallization.

Reformates or reformer effluents which are composed substantially of aromatic and paraffinic constituents can be prepared according to conventional techniques by contacting any suitable material such as naphtha charge material boiling in the range of about $C_5$ and preferably from about $C_6$ up to about 380° F. and higher with hydrogen at least initially in contact with any conventional reforming catalyst. This is a conventional reforming operation which involves a net production of hydrogen and is disclosed in greater detail in U.S. Pat. No. 3,395,094.

The process for upgrading reformates wherein ZSM-35 zeolite of ultimate particle diameter 0.005 to 0.1 micron is employed, generally involves contact during processing with a reformate or reformer effluent with or without added hydrogen, at a temperature between 500° F. and about 1100° F. and preferably between about 550° F and about 1000° F. The reactor pressure in such operation is generally within the range of about 25 and about 2000 psig and preferably about 50 to about 1000 psig. The liquid hourly space velocity, i.e., the liquid volume of hydrocarbon per hour per volume of catalyst is about 0.1 and about 250, and preferably between about 1 and 100. Although hydrogen is not essential to this process, when it is used the molar ratio of hydrogen to hydrocarbon charge employed is between about 0.1 and about 80 and preferably between about 1 and about 10.

It may be desirable in some instances to add a hydrogenation/dehydrogenation component to the ZSM-35 zeolite crystals. The amount of the hydrogenation/-dehydrogenation component employed is not narrowly critical and can range from about 0.01 to about 30 weight percent based on the entire catalyst. A variety of hydrogenation components may be combined with either the zeolite and/or matrix in any feasible manner which affords intimate contact of the components, employing well known techniques such as base exchange, impregnation, coprecipitation, cogellation, mechanical admixture of one component with the other and the like. The hydrogenation component can include metals, oxides and sulfides of metals of the Periodic Table which fall in Group VI-B including chromium, molybdenum, tungsten and the like; Group II-B including zinc and cadmium; Group VIII including cobalt, nickel, platinum, palladium, ruthenium, rhodium, osmium and iridium; Group IV-A such as germanium and tin and combinations of metals, sulfides and oxides of metals of Group VI-B and VIII, such as nickel-tungsten-sulfide, cobalt oxidemolybdenum oxide and the like.

The pre-treatment before use varies depending on the hydrogenation component present. For example, with components such as nickel-tungsten, cobalt-molybdenum, platinum and palladium, the catalyst may desirably be sulfided. With metals like platinum or palladium, a hydrogenation step may also be employed. These techniques are well known in the art and are accomplished in a conventional manner.

Catalyst made with small size ZSM-35 crystals (0.005–0.1 micron in ultimate particle, i.e., individual crystallite diameter) ages at a significantly slower rate than corresponding ZSM-35 containing catalysts of appreciably larger crystallite size (1 to 2 micron in ultimate diameter, i.e. individual crystallite diameter). This superior stability may be used to achieve improved yield-octane through use of decreased hydrogen/hydrogenation ratio while retaining satisfactory aging.

DESCRIPTION OF SPECIFIC EMBODIMENTS

The following examples will serve to illustrate the process of the invention without limiting the same:

EXAMPLE 1

A reaction mixture was prepared from the following reactants:

| Silicate Solution: | |
|---|---|
| Q Brand Sodium Silicate | 4060 g. |
| (28.9 wt. % SiO₂) | |
| (8.9 wt. % Na₂O) | |
| (62.2 wt. % H₂O) | |
| Water | 4000 g. |
| Daxad 27 (Sodium salts of polymerized substituted benzoid alkyl sulfonic acids combined with an inert material) | 20 g. |
| Acid Alum Solution: | |
| Al₂(SO₄)₃ . XH₂O | 378.4 g. |
| H₂SO₄ | 252.4 g. |
| NaCl | 800 g. |
| H₂O | 6500 g. |
| Pyrrolidine | 1000 g. |
| Water (added to autoclave prior to gelling) | 200 g. |

The silicate and acid alum solutions were changed to an autoclave simultaneously to form a gel. The gel was whipped for one hour at 250 RPM agitation. Pyrrolidine was added to the whipped gel. The resulting mixture was heated at 220° F. for 72 hours with 250 RPM agitation. The final product was filtered, washed and dried. X-ray diffraction analysis showed the product to be ZSM-35. Crystal sizes of the product were shown to be 0.02 to 0.04 micron by electron microscopy. Chemical analysis of the sample was found to be:

| | Wt. % |
|---|---|
| SiO₂ | 91.4 |
| Al₂O₃ | 6.71 |
| Na | 0.03 |
| N | 1.77 |
| C | 7.51 |
| Ash | 86.7 |

The dried zeolite was precalcined at 1000° F. in flowing nitrogen for 3 hours, followed by ammonium nitrate exchange to reduce the sodium content of the zeolite. The sample was sized into 14/20 mesh and air calcined at 1000° F. for 3 hours. The final product of HZSM-35 was found to contain less than 0.01 weight percent sodium.

EXAMPLE 2

Ortho xylene isomerization was effected with the catalyst of Example 1 by conducting o-xylene over such catalyst at a pressure of 250 psig, a weight hourly space velocity of about 2.5 at a temperature within the approximate range of 550° to 700° F. for a period of 45 hours. The results including o-xylene conversion and product distribution are shown in the table below.

TABLE

| Hours on Stream | 3 | 21 | 25.5 | 28.7 | 45 |
|---|---|---|---|---|---|
| Pressure, psig | 520 | 520 | 520 | 520 | 520 |
| WHSV | 2.4 | 2.5 | 2.6 | 2.4 | 2.5 |
| Average Temp. ° F | 547 | 596 | 649 | 698 | 698 |
| Conversion of x-xylene | 38.9 | 56.4 | 65.5 | 57.0 | 41.2 |
| Product Distribution, % Wt. | | | | | |
| Benzene | .10 | .11 | .12 | .11 | .11 |
| Toluene | .93 | 1.63 | 3.79 | 3.06 | 1.24 |
| p-xylene | 6.9 | 14.2 | 17.1 | 15.3 | 11.8 |
| m-xylene | 26.2 | 29.0 | 40.5 | 34.8 | 26.7 |
| o-xylene | 61.1 | 43.7 | 34.5 | 43.0 | 58.8 |
| C₉+ | 4.7 | 1.4 | 4.0 | 3.8 | 1.2 |

From the above results, it will be seen that small crystal HZSM-35 readily catalyzes the isomerization of o-xylene in the liquid phase (below about 600° F) as well as in the vapor phase.

EXAMPLE 3

A batch of ZSM-35 was prepared as follows:
Two solutions were prepared according to the following formula:

| Silicate solution: | Q-Brand | 1376.7 g. |
|---|---|---|
| | H₂O | 830 g. |
| Acid alum solution: | Al₂(SO₄)₃ . 14H₂O | 128.3 g. |
| | H₂SO₄ | 85.6 g. |
| | H₂O | 800 g. |

The clear acid alum solution was added to the silicate solution in a Waring blender. The mixture was whipped for 15 minutes into a thick gel. Another 1200 ml of water was added to dilute the gel. The gel was then transferred to an autoclave and 200 grams of pyrrolidine were added and mixed into the gel. The crystallization was carried out at 300° F with agitation. The gel mixture was completely crystallized after about 4 days according to x-ray diffraction analysis. The crystallizer slurry was discharged, filtered, washed and oven dried at 230° F for at least 4 hours. The zeolite product identified by x-ray diffraction analysis as ZSM-35 was analyzed and found to have the following composition:

| | Wt. % |
|---|---|
| SiO₂ | 93.4 |
| Al₂O₃ | 5.93 |
| Na | 0.30 |
| N | 2.06 |
| C | 8.14 |

-continued

| | Wt. % |
|---|---|
| Ash | 87.7 |

Crystallite size of the ZSM-35 was approximately 0.1–0.4 micron.

EXAMPLE 4

Propylene oligomerization was carried out at atmospheric prssure in the presence of the catalysts of Examples 1 and 3, i.e. the small crystallite size and larger crystallite size ZSM-35. In each instance, the catalyst, in the form of pellets of 14 to 25 mesh size, was placed in a rector equipped with a thermowell and calcined in air at 1000° F. for one hour and then purged with nitrogen while the temperature was lowered to 600° F. Propylene was passed over the catalyst at a rate of 1 liter per hour. Temperature adjustment, necessary because of the isotherm, was made so that the middle of the bed was maintained at about 600° F. The weight hourly space velocity was 7.7–8.4.

The conversion and product distribution results obtained are shown below:

| | Catalyst of Example 1 (.02 – .04μ) | Catalyst of Example 3 (0.1 – 0.4μ) |
|---|---|---|
| Propylene Converted | 98.7 | 65.3 |
| Product Distribution of Converted Charge | | |
| $C_5+$ | 90.9 | 90.9 |
| $C_4$ Fraction | 7.1 | 6.1 |
| $C_4+$ | 98.0 | 97.0 |
| $C_3$ (propane) | 0.1 | 3.0 |
| $C_1+C_2$ | 1.9 | 0 |

From the above results, it will be evident that the small crystal ZSM-35 provided an unexpectedly higher propylene conversion compared with the larger crystal ZSM-35.

It is to be understood that the foregoing description is merely illustrative of preferred embodiments of the invention of which many variations may be made by those skilled in the art within the scope of the following claims without departing from the spirit thereof.

We claim:

1. A process for hydrocarbon conversion which comprises contacting a containing a hydrocarbon charge under conversion conditions with a catalyst comprising a ZSM-35 crystalline zeolite characterized by an ultimate crystallite diameter of 0.005 to 0.1 micron as crystallized.

2. The process of claim 1 wherein said hydrocarbon conversion entails alkylation of aromatic hydrocarbons.

3. The process of claim 1 wherein said hydrocarbon conversion entails oligomerization of olefins.

4. The process of claim 1 wherein said hydrocarbon conversion entails xylene isomerization.

5. The process of claim 1 wherein the catalyst comprises a product resulting from thermal treatment of the ZSM-35 crystalline zeolite.

6. The process of claim 2 which involves alkylation at a temperature between about 400° and about 1000° F, a pressure between about 25 and about 1000 psig employing an aromatic hydrocarbon/alkylating agent mol ratio between about 2 and about 200 and an alkylating weight hourly space velocity between about 0.5 and about 50 , wherein said alkylating agent is an alkyl halide, an alcohol or an olefin.

7. The process of claim 3 which involves oligomerization at a temperature between about 550° and about 1150° F, a pressure between about 0.01 and about 1000 psig, employing a weight hourly space velocity between about 0.1 and about 1000.

8. The process of claim 4 which involves isomerization at a temperature between about 300° and about 900° F, a pressure between about 25 and about 1000 psig, employing a weight hourly space velocity between about 0.2 and about 100.

9. The process of claim 1 wherein said catalyst comprises ZSM-35 in the acid form.

* * * * *

UNITED STATES PATENT AND TRADEMARK OFFICE
CERTIFICATE OF CORRECTION

PATENT NO. : 3,992,466
DATED : November 16, 1976
INVENTOR(S) : CHARLES J. PLANK, EDWARD J. ROSINSKI and ALBERT B. SCHWARTZ It is certified that error appears in the above-identified patent and that said Letters Patent are hereby corrected as shown below:

Column 3, line 66, "ZSMk-35" should be --ZSM-35--.

Column 5, line 42, "crystalline" should be --crystallite--.

Column 7, line 37, "(8.9 wt. % NaO)" should be --(8.9 wt. % $Na_2O$)--.

Column 8, line 13, "250" should be --520--.

Column 10, line 8, "contacting a containing a hydrocarbon charge" should read --contacting a charge containing a hydrocarbon--.

Signed and Sealed this

Eighth Day of March 1977

[SEAL]

Attest:

RUTH C. MASON
Attesting Officer

C. MARSHALL DANN
Commissioner of Patents and Trademarks